US00PP13656P29

(12) United States Plant Patent
Koppe

(10) Patent No.: US PP13,656 P2
(45) Date of Patent: Mar. 11, 2003

(54) BEGONIA PLANT NAMED 'BETULIA LIGHT'

(75) Inventor: Lubbertus H. Koppe, Ermelo (NL)

(73) Assignee: Koppe Veredeling B.V., Ermelo (NL)

( * ) Notice: Subject to any disclaimer, the term of this patent is extended or adjusted under 35 U.S.C. 154(b) by 0 days.

(21) Appl. No.: 10/077,377

(22) Filed: Feb. 15, 2002

(51) Int. Cl.[7] ..... A01H 5/00

(52) U.S. Cl. ..... Plt./344

(58) Field of Search ..... Plt./344, 345

(56) References Cited

PUBLICATIONS

UPOV–ROM GTITM Computer Database 2002/03, GTI Jouve Retrieval Software, Citation for Begonia 'Betulia Light'.*

* cited by examiner

*Primary Examiner*—Bruce R. Campell
*Assistant Examiner*—June Hwu
(74) *Attorney, Agent, or Firm*—C. A. Whealy

(57) ABSTRACT

A new and distinct cultivar of Begonia plant named 'Betulia Light', characterized by its upright and mounded plant habit; single to semi-double flowers that are white in color with pink centers and held above the foliage; and excellent postproduction longevity.

1 Drawing Sheet

BOTANICAL CLASSIFICATION/CULTIVAR DESIGNATION

*Begonia×hybrida* cultivar Betulia Light.

BACKGROUND OF THE INVENTION

The present Invention relates to a new and distinct cultivar of Begonia plant, botanically known as *Begonia×hiemalis*, commercially known as Elatior Begonia, and hereinafter referred to by the name 'Betulia Light'.

The new Begonia was discovered by the Inventor in a controlled environment in Ermelo, The Netherlands, in March, 1999, as a naturally-occurring whole plant mutation of *Begonia×hiemalis* 'Betulia', disclosed in U.S. Plant Pat. No. 10,475. The new Begonia was observed as a single plant in a group of flowering plants of the parent cultivar. The selection of this plant was based on its flower coloration.

Asexual reproduction of the new Begonia by cuttings taken in a controlled environment in Ermelo, The Netherlands, has shown that the unique features of this new Begonia are stable and reproduced true to type in successive generations.

SUMMARY OF THE INVENTION

The cultivar 'Betulia Light' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Betulia Light'. These characteristics in combination distinguish 'Betulia Light' as a new and distinct Begonia:

1. Upright and mounded plant habit.

2. Single to semi-double flowers that are white in color with pink centers and held above the foliage.

3. Excellent postproduction longevity.

Plants of the new cultivar are most similar to plants of the parent, the cultivar Betulia. Plants of the new cultivar differ from plants of the cultivar Betulia primarily in flower color as plants of the cultivar Betulia have red-colored flowers.

BRIEF DESCRIPTION OF THE PHOTOGRAPH

The accompanying colored photograph illustrates the overall appearance of the new Begonia, showing the colors as true as it is reasonably possible to obtain in colored reproductions of this type. Colors in the photograph may differ slightly from the color values cited in the detailed botanical description which accurately describe the colors of the new Begonia. The photograph comprises a side perspective view of a typical flowering plant of 'Betulia Light'.

DETAILED BOTANICAL DESCRIPTION

In the following description, color references are made to The Royal Horticultural Society Colour Chart, 1995 Edition, except where general terms of ordinary dictionary significance are used. The aforementioned photograph and following observations and measurements describe plants grown in Ermelo, The Netherlands, under commercial practice in a glass-covered greenhouse. Average day and night temperatures were about 20° C. during the first three to four weeks then lowered to an average day and night temperature of 19° C. until flowering. Four weeks after planting rooted cuttings in 12-cm containers, one week of long nyctoperiods of 16 hours was given followed by short nyctoperiods of eight hours until flowering. Plants used for the photographs and the description were about four months old. Measurements and numerical values represent averages for typical flowering plants.

Botanical classification: *Begonia×hiemalis* cultivar Betulia Light.

Commercial classification: Elatior Begonia.

Parentage: Naturally-occurring whole plant mutation of *Begonia×hiemalis* cultivar Betulia, disclosed in U.S. Plant Pat. No. 10,475.

Propagation:

*Type.*—Cuttings.

*Time to develop roots.*—About 40 days at temperatures of 20 to 22° C.

*Root description.*—Fine, fibrous, well-branched and spreading. Plants of the new Begonia have not been observed to form tubers.

Plant description:

*Plant form.*—Upright and mounded plant habit, inverted triangle; freely branching with good stem and stem base strength. Flowers are single to semi-double and abundant. Plants flower continuously.

*Growth habit.*—Moderate growth rate, vigorous. Suitable for 12 to 15-cm containers. Under optimal environmental and cultural conditions, usually about four months are required to produce proportional 13-cm potted plants from cuttings. Vegetative shoots are formed at basal nodes and flowering shoots are formed at upper nodes.

*Plant height.*—About 23 cm.

*Plant width.*—About 38 cm.

*Leaves.*—Arrangement: Simple, alternate. Young leaves, length: About 5.25 cm. Young leaves, width: About 6 cm. Fully expanded leaves, length: About 7.8 cm. Fully expanded leaves, width: About 10 cm. Shape: Asymmetrical, more or less reniform. Apex: Acuminate. Base: Cordate. Margin: Doubly serrate. Texture: Glabrous, smooth. Venation pattern: Palmate. Color: Young leaves, upper surface: Darker than 147A. Young leaves, lower surface: 194C. Fully expanded leaves, upper surface: Much darker than 147A. Fully expanded leaves, lower surface: 194C. Venation, upper surface: 147B. Venation, lower surface: 147C. Petiole length: About 4.25 cm. Petiole texture: Pubescent. Petiole color: 180A to 180B.

Flower description:

*Flowering habit.*—Single to semi-double flowers with numerous tepals arranged in axillary cymes. Usually 5 to 13 flowers per cyme. Many cymes in flower simultaneously. Flowers positioned above the foliage. Flowering continuous.

*Natural flowering season.*—Plants will flower year around regardless of nyctoperiod, however plants flower earlier and more abundantly from mid-February until November in the Northern Hemisphere.

*Flowers.*—Shape: Rounded. Diameter: About 4.5 cm. Depth (height): About 1 cm.

*Flower buds.*—Length: About 1.4 cm. Diameter: About 1.1 cm. Color: 155A.

*Tepals.*—Arrangement: Rosette. Shape: Rounded flabellate. Apex: Rounded. Margin, outer and inner tepals: Slightly crenate. Quantity per flower: Usually about 4 to 9 per flower. Size: Outer tepals: Length: About 2.75 cm. Width: About 2 cm. Inner tepals: Length: About 2.2 cm. Width: About 2 cm. Texture: Smooth, satiny, glabrous. Color:

When opening, outer and inner tepals, upper and lower surfaces: 155D, towards base, 55B. Fully opened, outer and inner tepals, upper surface: 155D, towards base, 55C; flower color does not fade with subsequent development. Fully opened, outer tepals, lower surface: 4D. Fully opened, inner tepals, lower surface: 56D.

*Flower bracts.*—Arrangement: Two, opposite. Shape: Broadly cordate. Apex: Apiculate. Margin: Serrate. Texture: Glabrous. Color, both surfaces: 145A.

*Peduncles.*—Angle: Erect. Length: About 4.75 cm. Texture: Slightly pubescent. Color: 180D.

*Pedicels.*—Angle: Erect. Length: About 2.9 cm. Texture: Glabrous, smooth. Color: 180D.

*Reproductive organs.*—Stamens: None observed. Pistils: None observed.

*Seed.*—Seed production has not been observed as reproductive organs are not formed.

Postproduction longevity:

*Individual flowers.*—Generally about 2 to 3 weeks.

*Whole plants.*—About 6 weeks under interior conditions.

Disease/pest resistance: Resistance to pathogens and pests common to Begonia has not been observed.

It is claimed:

1. A new and distinct cultivar of Begonia plant named 'Betulia Light', as illustrated and described.

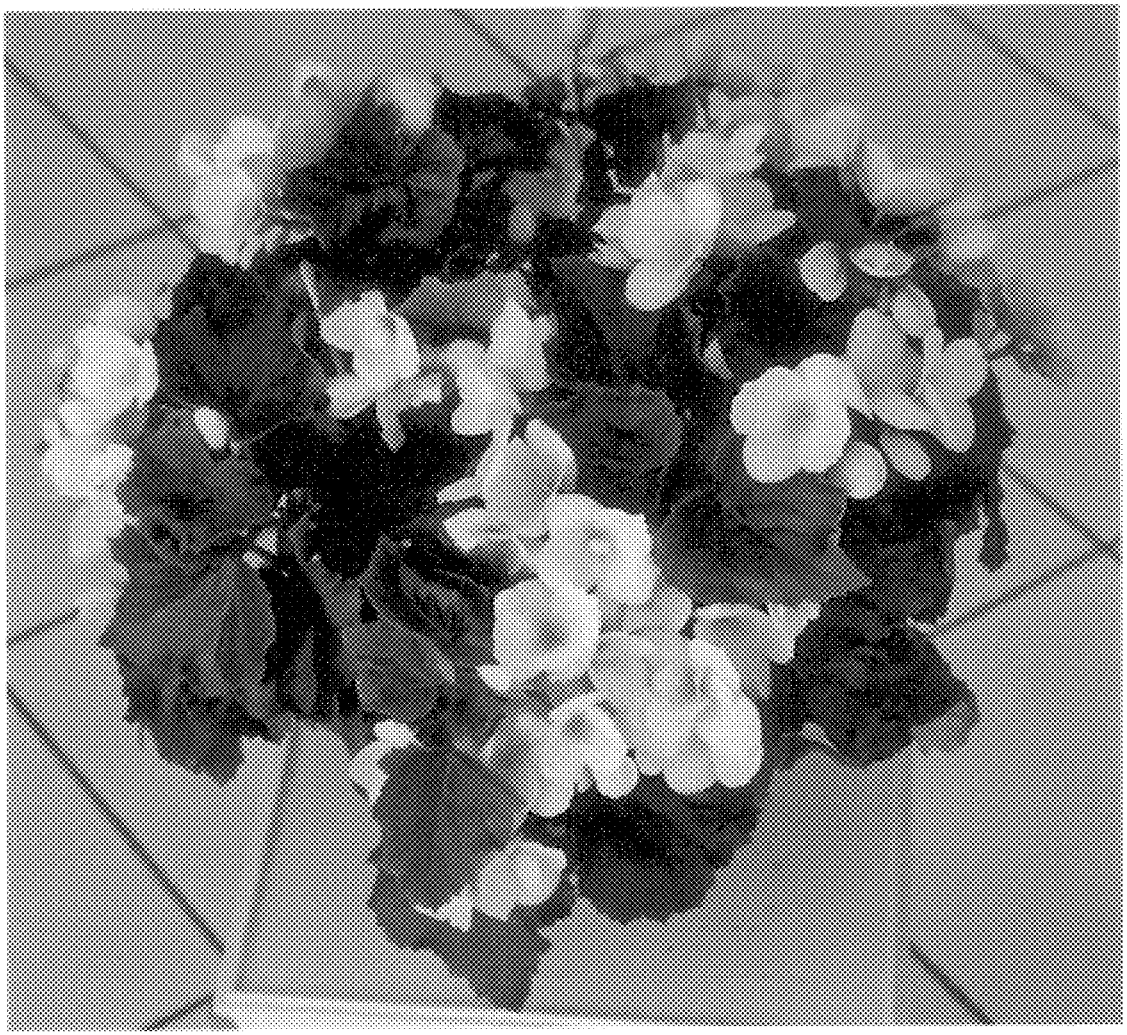

* * * * *